United States Patent
Gerdinand et al.

(10) Patent No.: US 10,875,823 B2
(45) Date of Patent: Dec. 29, 2020

(54) METHOD FOR PRODUCING N-METHYL-P-TOLUIDINE FOR USE AS AN ADDITIVE FOR AVIATION GASOLINE

(71) Applicant: LANXESS DEUTSCHLAND GMBH, Cologne (DE)

(72) Inventors: Martina Gerdinand, Bergisch Gladbach (DE); Rainer Dost, Langenfeld (DE); Ralf Krahwinkel, Langenfeld (DE); Hans-Jurgen Quella, Leverkusen (DE); Daniel Ullrich, Langenfeld (DE); Patrick Kurr, Monchengladbach (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 16/473,289

(22) PCT Filed: Dec. 19, 2017

(86) PCT No.: PCT/EP2017/083582
§ 371 (c)(1),
(2) Date: Jun. 25, 2019

(87) PCT Pub. No.: WO2018/127406
PCT Pub. Date: Jul. 12, 2018

(65) Prior Publication Data
US 2020/0148625 A1    May 14, 2020

(30) Foreign Application Priority Data

Jan. 5, 2017 (EP) .................... 17150428

(51) Int. Cl.
| | | |
|---|---|---|
| *C07C 209/18* | (2006.01) | |
| *C07C 211/48* | (2006.01) | |
| *B01J 23/72* | (2006.01) | |
| *B01J 35/02* | (2006.01) | |
| *B01J 37/03* | (2006.01) | |
| *B01J 37/04* | (2006.01) | |
| *B01J 37/06* | (2006.01) | |
| *B01J 37/02* | (2006.01) | |

(52) U.S. Cl.
CPC ............ *C07C 209/18* (2013.01); *B01J 23/72* (2013.01); *B01J 35/023* (2013.01); *B01J 37/0236* (2013.01); *B01J 37/031* (2013.01); *B01J 37/04* (2013.01); *B01J 37/06* (2013.01); *C07C 211/48* (2013.01); *C07C 2523/72* (2013.01)

(58) Field of Classification Search
CPC ...... C07C 209/18; C07C 211/48; B01J 23/72; B01J 35/023; B01J 37/0236; B01J 37/031; B01J 37/04; B01J 37/06
USPC ........................................................ 564/401
See application file for complete search history.

(56) References Cited

U.S. PATENT DOCUMENTS

| | | |
|---|---|---|
| 2,580,284 A | 12/1951 | Deahl |
| 5,030,759 A | 7/1991 | Bayer |
| 5,068,434 A | 11/1991 | Klug |
| 5,097,071 A | 3/1992 | Immel |
| 5,166,440 A | 11/1992 | Immel |
| 7,119,237 B2 * | 10/2006 | Prinz .................. B01J 23/80 568/885 |
| 8,901,354 B2 | 12/2014 | Shi et al. |
| 9,688,646 B2 | 6/2017 | Shi et al. |
| 10,226,760 B2 | 3/2019 | Paulus et al. |
| 2003/0187309 A1 | 10/2003 | Prinz |
| 2017/0051226 A1 | 2/2017 | Obrecht et al. |

FOREIGN PATENT DOCUMENTS

| | | |
|---|---|---|
| CN | 101792393 B | 4/2013 |
| CN | 106957232 A | 7/2017 |
| CN | 108658783 A | 10/2018 |
| RU | 2205067 C1 | 5/2003 |
| RU | 2223258 C1 | 2/2004 |
| RU | 2270187 C2 | 2/2006 |
| RU | 2274488 C1 | 4/2006 |
| RU | 2346740 C1 | 2/2009 |

OTHER PUBLICATIONS

M. Vijayaraj, et al.: "Selective mono-N-methylation of aniline substrates on Cu,1-x>Zn<x>Fe<2>O<4>", Applied Catalysis A: General, Bd 320, Jan. 4, 2007, Elsevier, Amsterdam, NL.
Brown Jerome E. et als., "Mechanism of aromatic amine anti-knock action", Industrial and Engineering Chemistry, vol. 47, No. 10, Oct. 1955, American Chemical Society, pp. 2141-2146.

* cited by examiner

Primary Examiner — Yong L Chu
(74) Attorney, Agent, or Firm — Nicanor A. Kohncke; Christopher L. McDavid

(57) ABSTRACT

The invention relates to novel methods for preparing N-methyl-p-toluidine for the use thereof as additive for aviation fuel, and to specific catalysts for these methods.

12 Claims, 1 Drawing Sheet

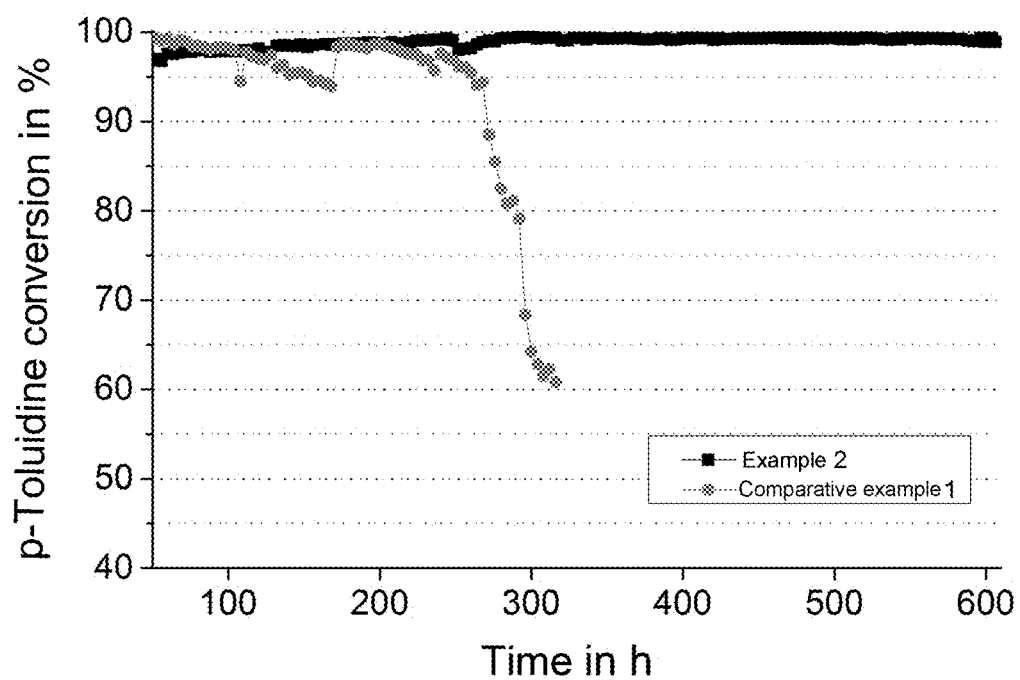

METHOD FOR PRODUCING N-METHYL-P-TOLUIDINE FOR USE AS AN ADDITIVE FOR AVIATION GASOLINE

The invention relates to novel methods for preparing N-methyl-p-toluidine for the use thereof as additive for aviation fuel, and to specific catalysts for these methods.

Alkylated aromatic amines have high economic potential and are used for example as fuel additives (antiknock agents) in fuels in order to replace environmentally harmful lead-containing additives. The most commonly used alkylated aromatic amine is N-methylaniline. However, N-alkylated m- and p-toluidines may also be used. For the preparation of N-methylated toluidines, and especially N-methyl-p-toluidine, only few economically relevant methods have been described. U.S. Pat. No. 5,030,759 and DE-A3803661 describe the N-alkylation of aniline and toluidines over zeolite catalysts. U.S. Pat. No. 2,580,284 describes the N-alkylation of aniline over aluminium oxide-based supported catalysts, which contain, as catalytically active element, copper and promoters such as zinc oxide or calcium oxide. DE-A3942413 discloses the use of pure niobic acid or niobic acid in a mixture with inert solids such as titanium oxide, zinc oxide, etc., which however leads to relatively high proportions of dialkylated products. DE-A3840194 describes the use of aluminium oxide-supported copper catalysts, which are impregnated with manganese or rare-earth compounds. The main issue in the examples described above is the short service life of the catalysts used to date, which is caused by formations of by-product on the catalyst surface. For example, RU-2205067 reports a maximum service life of 230 hours for the N-methylation of aniline when using a Cu/Mn/Cr/Fe/Co supported catalyst on aluminium oxide. In RU-2274488, running times of up to at most 470 hours are reported with similar systems. As an alternative to this, RU-2270187 and RU-2223258 disclose the preparation of N-methylaniline via regenerating N-methylation of the aniline with methanol and by catalytic hydrogenation of the nitrobenzene with hydrogen and subsequent alkylation with methanol over $CuO/Cr_2O_3/Al_2O_3$ catalysts. However, the methods are all, economically and/or environmentally, in need of improvement, since firstly only low throughputs are achieved and secondly many catalysts contain carcinogenic components.

It was therefore an object of the present invention to provide a method for preparing N-methyl-p-toluidine in high yields, a long service life of the catalyst with high throughput and avoidance of carcinogenic metals or oxides thereof, and ideally to provide a novel, economically producible catalyst.

It has surprisingly now been found that the object of the invention can be achieved by using at least one catalyst which at least contains, in the following proportions, Cu: 45.5-68.0% by weight, preferably 47.0-64.1% by weight, particularly preferably 47.5-60.5% by weight, Zn: 12.3-22.5% by weight, preferably 14.3-21.5% by weight, particularly preferably 15.2-19.5% by weight, Al: 1.9-4.1% by weight, preferably 2.2-3.8% by weight, particularly preferably 2.5-3.6% by weight, and 7.8-28.2% by weight of oxygen, preferably 13.6-25.1% by weight, particularly preferably 16.2-24.5% by weight, of oxygen and optionally 0-10% by weight of carbon, wherein Cu, Zn, Al, oxygen and, if present, carbon comprise at least 99% by weight, preferably 99.5% by weight, of the total amount of the catalyst.

The present invention therefore provides methods for preparing N-methyl-p-toluidine by reacting p-toluidine with methanol, according to which methods at least one catalyst is used which at least contains, in the following proportions, Cu: 45.5-68.0% by weight, preferably 47.0-64.1% by weight, particularly preferably 47.5-60.5% by weight, Zn: 12.3-22.5% by weight, preferably 14.3-21.5% by weight, particularly preferably 15.2-19.5% by weight, Al: 1.9-4.1% by weight, preferably 2.2-3.8% by weight, particularly preferably 2.5-3.6% by weight, and 7.8-28.2% by weight of oxygen, preferably 13.6-25.1% by weight, particularly preferably 16.2-24.5% by weight, of oxygen and optionally 0-10% by weight of carbon, wherein Cu, Zn, Al, oxygen and, if present, carbon comprise at least 99% by weight, preferably 99.5% by weight, of the total amount of the catalyst.

Other constituents of the catalyst may for example be alkali metals and alkaline earth metals, water or nitrogen compounds, such as for example nitrates.

In one preferred embodiment, the catalyst at least contains, in the following proportions, copper oxide-containing compounds, calculated as CuO 59.1-78.3% by weight, particularly preferably 62.3-74.8% by weight, ZnO: 15.3-27.8% by weight, particularly preferably 17.5-25.2% by weight, $Al_2O_3$: 4.4-6.8% by weight, particularly preferably 4.9-6.1% by weight, and 0-10% by weight of carbon, wherein CuO, ZnO, $Al_2O_3$ and, if present, carbon comprise at least 99% by weight, preferably 99.5% by weight, of the total amount of the catalyst.

In one embodiment of the invention, the catalyst is pretreated by supplying hydrogen, preferably in the presence of an inert gas, at temperatures of at least 150° C.

The pretreatment of the catalyst with hydrogen can take place prior to introduction into the reactor or in the reactor itself, i.e. in the reactor which is used for preparing N-methyl-p-toluidine.

Pretreatment of the catalyst preferably takes place by introducing the catalyst into a reduction apparatus and heating it therein to preferably 150-300° C., particularly preferably 200-300° C. and very particularly preferably to 240-290° C. Preferably, the catalyst is contacted with a nitrogen/hydrogen stream of an initial composition of 95% $N_2$ and 5% $H_2$. The proportion of hydrogen in the gas stream is preferably increased to 100%. The abovementioned pretreatment generally results in CuO being reduced to elemental Cu, while the other metals are present as oxides.

For the pretreatment of the catalyst with hydrogen in the reactor itself, the catalyst is heated in the abovementioned reactor, under a nitrogen/hydrogen stream, preferably of the initial composition of 95% $N_2$ and 5% $H_2$, with preference to 150-300° C., preferably 200-300° C. and particularly preferably to 240-290° C., and then the proportion of hydrogen in the gas stream is preferably increased to 100% $H_2$.

In one preferred embodiment of the method according to the invention, the catalyst loading is 0.1 to 1.5, preferably 0.3 to 1, particularly preferably 0.4 to 0.7, kg of p-toluidine per kg of catalyst per hour.

In the method according to the invention for preparing N-methyl-p-toluidine, p-toluidine of commercial quality may be used, for example from LANXESS Deutschland GmbH.

In the method according to the invention for preparing N-methyl-p-toluidine, methanol of commercial quality may be used, for example from Brenntag GmbH.

In the method according to the invention, the reaction preferably proceeds in a tubular reactor.

In one further preferred embodiment of the method according to the invention, the molar ratio of p-toluidine to methanol is 1:0.7 to 1:5, preferably 1:1 to 1:3.5, particularly preferably 1:1.5 to 1:2.5.

In one likewise preferred embodiment of the method according to the invention, the molar ratio of p-toluidine to hydrogen is 1:0.1 to 1:5, preferably 1:1 to 1:3.5, particularly preferably 1:1 to 1:3.

In one further embodiment, the hydrogen formed in the reaction, for example by the decomposition of methanol, may be recycled to the reactor in a gas circuit in a mixture with the other process gases.

In one further preferred embodiment of the method according to the invention, the method is carried out at a temperature of 200 to 300° C., preferably 210 to 270° C., particularly preferably 220 to 250° C.

The present invention further provides a method for producing a catalyst containing Cu, Zn and Al by addition of aqueous sodium carbonate solution and a mixture of aqueous copper nitrate and zinc nitrate solution to an aqueous suspension of aluminium oxide, while maintaining a pH of preferably 7.5-8.5, particularly preferably 7.9-8.1, at a temperature of 60-80° C., preferably at 65-75° C., wherein the mixture of aqueous copper nitrate and zinc nitrate solution is adjusted before the addition to a pH of <1, preferably a pH of 0.4-0.6 (at 20° C.), the resulting suspension containing Cu, Zn and Al is subsequently washed, then dried, the solid obtained therefrom is calcined and preferably tabletted.

The adjustment of the pH to <1, preferably a pH of 0.4-0.6, preferably takes place using nitric acid.

The amounts of aluminium oxide suspension, zinc nitrate solution and copper nitrate solution used depend on the desired composition of the catalyst containing Cu, Zn and Al.

After precipitation is complete, the suspension is preferably initially concentrated over a crossflow filter, and then washed continuously over the crossflow filter with deionized water.

In one preferred embodiment of the invention, the resulting suspension is subsequently filtered, washed, and the solid dried in a drying cabinet and preferably subsequently sieved. As an alternative, the solid may also be dried by spray drying. The powder obtained is preferably calcined in a rotary kiln at 270-550° C., subsequently admixed with graphite and processed into mouldings using a tabletting press.

The catalyst produced in accordance with the method according to the invention is preferably used for preparing N-methyl-p-toluidine.

The present invention moreover provides the catalyst produced in accordance with the method according to the invention, having a specific copper surface area of 1.4-10.2 m$^2$/g, measured to DIN66131-3.

The present invention moreover provides the catalyst produced in accordance with the method according to the invention, having an average copper particle size of more than 30 nm, preferably 35-100 nm, particularly preferably 35-75 nm, measured to DIN66131-3.

The catalyst preferably has the following composition prior to the pretreatment and at least contains, in the following proportions, Cu: 45.5-68.0% by weight, preferably 47.0-64.1% by weight, particularly preferably 47.5-60.5% by weight, Zn: 12.3-22.5% by weight, preferably 14.3-21.5% by weight, particularly preferably 15.2-19.5% by weight, Al: 1.9-4.1% by weight, preferably 2.2-3.8% by weight, particularly preferably 2.5-3.6% by weight, and 7.8-28.2% by weight of oxygen, preferably 13.6-25.1% by weight, particularly preferably 16.2-24.5% by weight, of oxygen and optionally 0-10% by weight of carbon, wherein Cu, Zn, Al, oxygen and, if present, carbon comprise at least 99% by weight, preferably 99.5% by weight, of the total amount of the catalyst.

The present invention further provides N-methyl-p-toluidine having a p-toluidine content >0.0001 to <10% by weight, preferably >0.001 to <1% by weight, which has preferably been prepared in accordance with the method according to the invention.

In addition to the p-toluidine in proportions of >0.0001 to <10% by weight, preferably >0.001 to <1% by weight, the N-methyl-p-toluidine according to the invention preferably also contains N,N-dimethyl-p-toluidine in proportions of preferably >0.0001 to <5% by weight.

N-methyl-p-toluidine having a p-toluidine content >0.0001 to <10% by weight, optionally in the presence of N,N-dimethyl-p-toluidine, is distinguished, in combination with a standard aviation base fuel, by a freeze point of less than −58° C., according to ASTM D23866, and is therefore outstandingly suitable as additive for use in lead-free aviation fuel (avgas) according to ASTM D910.

In order to comply with the regulations required for avgas in respect of vapour pressure and boiling points, the hydrocarbons typically used for aviation base fuel have a carbon number of the order of magnitude of from four (butane) to ten, with a predominant prevalence of eight (isooctane).

Moreover, the hydrocarbon components of a standard aviation base fuel typically contain isoparaffinic hydrocarbons (butane, pentane, hexane, heptane and octane isomers) and aromatic hydrocarbons (benzene, toluene, ethylbenzene, xylene isomers, trimethylbenzene, cumene and naphthalene).

Standard aviation base fuel is described, for example, in Chevron Aviation Fuels Technical Review 2M CBRES GIDC 5723 10/06 MS-9891 (10/06).

The present invention further provides for the use of the N-methyl-p-toluidine according to the invention and also of the N-methyl-p-toluidine prepared in accordance with the method according to the invention as additive for fuels, preferably aviation fuel.

The scope of the invention encompasses all hereinabove and hereinbelow recited definitions, indices, parameters and elucidations, which are of a general nature or are mentioned in preferred ranges, in any combination with one another, i.e. including between the respective ranges and preferred ranges.

The examples which follow serve to elucidate the invention without having any limiting effect.

EXAMPLES

Example 1

Production of the catalyst according to the invention:
Preparation:
Charge 1:
18 773 g of copper nitrate solution with 14.6% Cu and 5522 g of zinc nitrate solution with 15.9% Zn were made up to 22 400 ml with distilled water. The pH was then adjusted to 0.5 with HNO$_3$.
Charge 2:
8959 g of sodium carbonate were dissolved in 31 038 g of water.
Procedure:
The contents of the precipitation vessel, consisting of 40 000 g of deionized water, were heated to 70° C. using a thermostat. Charges 1 and 2 were likewise heated to 70° C. 273.6 g of aluminium oxide were added to the precipitation vessel with stirring. The mixture of copper nitrate and zinc nitrate solution from Charge 1 was pumped continuously (190-220 ml/min) into the precipitation vessel using a diaphragm pump, while a second diaphragm pump supplied the sodium carbonate solution from Charge 2 by pumping, with the result that the pH was held at 7.9-8 during the precipitation.

The suspension was subsequently concentrated on a crossflow filter and washed with deionized water to a conductivity <100 µS.

The suspension was filtered with suction over a porcelain suction filter. The filter cake was dried in a drying cabinet at 110° C. and pressed through a 0.8 mm sieve. The product was calcined in a rotary kiln at 450° C.

4505 g of the calcined product were processed with 225 g of graphite into 5×5 mm tablets on a tabletting press (Korsch XL 100).

Physical Properties:
Bulk density: 1746 g/l,
Ø lateral fracture hardness: 168 N,
BET surface area: 65.4 m$^2$/g, determined to ISO9277,
Pore volume: 0.163 cm$^3$/g,
Loss on ignition (1 h, 900° C.): 10.7%,
Specific Cu surface area: 5.8 m$^2$/g, measured to DIN 66131-3,
Average copper particle size: 54.8 nm, measured to DIN 66131-3.

The composition of the catalyst gave the following values:
Cu: 51.0% by weight, Zn: 16.3% by weight, Al 2.7% by weight, O: 23.8% by weight, which changed after heating to 900° C. and a hold time of 1 h as follows:
Cu: 57.0% by weight, Zn: 18.3% by weight, Al: 2.9% by weight, O: 21.4% by weight Example 2

Testing of the catalyst according to the invention: 81 ml of the catalyst produced in accordance with Example 1 (screen fraction 1.6-3.15 mm) were introduced into a reaction tube having an internal diameter of 32 mm and a length of 180 mm, additionally containing an internal tube with thermocouple. The reaction tube was maintained at 275° C. using an electrical heating means, wherein the catalyst was initially pretreated with a mixture of nitrogen and hydrogen. Subsequently, a reaction mixture of 40.4 g/h of p-toluidine, 24.1 g/h of methanol and 25.4 l/h of hydrogen was metered in continuously. The reaction product was condensed and analysed by gas chromatography.

The composition of the mixture, after subtraction of water and methanol and measured after 300 hours, was:
p-toluidine: 0.48% by weight
N-methyl-p-toluidine: 96.27% by weight
N,N-dimethyl-p-toluidine: 3.25% by weight
and after 600 h:
p-toluidine: 0.59% by weight
N-methyl-p-toluidine: 97.67% by weight
N,N-dimethyl-p-toluidine: 1.74% by weight
Even after 600 hours of running time, no significant deactivation of the catalyst was apparent.

Comparative Example 1

Production of the catalyst analogously to U.S. Pat. No. 2,580,284:
209.5 g of aluminium oxide were admixed with 113 ml of an impregnation solution consisting of 94.33 g of calcium nitrate*4H$_2$O and 48.7 g of copper(II) nitrate*3H$_2$O dissolved in 34 g of water. After impregnation, the material was dried in a hot air dryer at 120° C. and subsequently calcined for 4 hours at 450° C. 243.9 g of catalyst having proportions of metals of 5.17% by weight of Cu and 6.46% by weight of Ca on aluminium oxide were obtained.

Testing of the Catalyst:
81 ml of the catalyst produced in accordance with Comparative Example 1 were used analogously to Example 1 for the alkylation of p-toluidine.

The typical composition of the mixture, after subtraction of water and methanol and measured after 300 hours, was:
p-toluidine: 33.02% by weight
N-methyl-p-toluidine: 66.70% by weight
N,N-dimethyl-p-toluidine: 0.28% by weight The direct comparison of the two catalysts is represented in FIG. 1. It is clearly apparent that the catalyst used according to the prior art has a service life of less than 300 hours, whereas the catalyst according to the invention displays no deactivation even after 600 hours.

What is claimed is:

1. A method for preparing N-methyl-p-toluidine, comprising:
reacting p-toluidine with methanol in the presence of at least one catalyst, wherein the at least one catalyst comprises, in the following proportions,
Cu: 45.5-68.0% by weight,
Zn: 12.3-22.5% by weight,
Al: 1.9-4.1% by weight,
and 7.8-28.2% by weight of oxygen, wherein Cu, Zn, Al and oxygen comprise at least 99% by weight, of the total amount of the catalyst.

2. The method according to claim 1, wherein the catalyst is pretreated by supplying hydrogen at temperatures of at least 150° C.

3. The method according to claim 2, wherein the pretreatment of the catalyst with hydrogen can take place prior to introduction into the reactor or in the reactor itself.

4. The method according to claim 1, wherein the catalyst loading is 0.1 to 1.5 kg of p-toluidine per kg of catalyst per hour.

5. The method according to claim 1, wherein the molar ratio of p-toluidine to methanol is 1:0.7 to 1:5.

6. The method according to claim 1, wherein the molar ratio of p-toluidine to hydrogen is 1:0.1 to 1:5.

7. The method according to claim 1, wherein the method is carried out at a temperature of 200 to 300° C.

8. The method according to claim 1, wherein the at least one catalyst comprises, in the following proportions,
Cu: 47.0-64.1% by weight,
Zn: 14.3-21.5% by weight,
Al: 2.2-3.8% by weight,
and 13.6-25.1% by weight, of oxygen and 0-10% by weight of carbon, wherein Cu, Zn, Al, oxygen and carbon comprise at least 99.5% by weight, of the total amount of the catalyst.

9. The method according to claim 1, wherein the at least one catalyst comprises, in the following proportions,
Cu: 47.5-60.5% by weight,
Zn: 15.2-19.5% by weight,
Al: 2.5-3.6% by weight,
and 16.2-24.5% by weight, of oxygen and 0-10% by weight of carbon, wherein Cu, Zn, Al, oxygen and carbon comprise at least 99.5% by weight, of the total amount of the catalyst.

10. The method according to claim 1, wherein the catalyst loading is 0.3 to 1 kg of p-toluidine per kg of catalyst per hour.

11. The method according to claim 1, wherein the molar ratio of p-toluidine to methanol is 1:1 to 1:3.5.

12. The method according to claim 1, wherein the molar ratio of p-toluidine to hydrogen is 1:0.5 to 1:4.

* * * * *